(12) United States Patent
Kofman

(10) Patent No.: US 7,487,664 B1
(45) Date of Patent: Feb. 10, 2009

(54) SYSTEM AND METHOD FOR SENSING A WIDE RANGE OF WATER VAPOR LEVELS IN AN ATMOSPHERE

(75) Inventor: Victor Kofman, Buffalo Grove, IL (US)

(73) Assignee: Illinois Instruments, Inc., Johnsburg, IL (US)

( * ) Notice: Subject to any disclaimer, the term of this patent is extended or adjusted under 35 U.S.C. 154(b) by 340 days.

(21) Appl. No.: 11/355,499

(22) Filed: Feb. 16, 2006

Related U.S. Application Data

(60) Provisional application No. 60/692,671, filed on Jun. 21, 2005.

(51) Int. Cl.
*G01M 3/04* (2006.01)
(52) U.S. Cl. .......................................... 73/40
(58) Field of Classification Search ...................... 73/40
See application file for complete search history.

(56) References Cited

U.S. PATENT DOCUMENTS

| | | | | |
|---|---|---|---|---|
| 5,876,664 | A | * | 3/1999 | Childers et al. ................ 422/28 |
| 6,910,341 | B2 | * | 6/2005 | Srichai et al. .................. 62/115 |

\* cited by examiner

*Primary Examiner*—Hezron Williams
*Assistant Examiner*—Rodney T Frank
(74) *Attorney, Agent, or Firm*—Jon Carl Gealow

(57) ABSTRACT

A dual sensor system for measuring the presence of a wide range of water vapor concentration in an atmosphere. A first sensor for measuring higher levels of water vapor concentration and a second sensor for measuring lower levels of water vapor concentration. A pair of three way valves operable to provide two flow paths for the atmosphere, a first path including both the first and second sensors, and a second path including only the second sensor. An electronic control arrangement for indicating the water vapor levels in the atmosphere and for providing an electronic signal to actuate the pair of three way valves.

12 Claims, 2 Drawing Sheets

SYSTEM AND METHOD FOR SENSING A WIDE RANGE OF WATER VAPOR LEVELS IN AN ATMOSPHERE

The following U.S. patent application is hereby incorporated by reference in its entirety for its teaching:

U.S. Provisional Patent Application Ser. No. 60/692,671 for System and Method for Sensing a Wide Range of Water Vapor Levels in an Atmosphere, filed Jun. 21, 2005.

FIELD OF THE INVENTION

The present invention relates to a system and method for more efficiently detecting and measuring a wide range of water vapor levels in an atmosphere. More particularly it relates to a system and method utilizing at least two sensors, each of which responds to a different range of levels of water vapor content in an atmosphere. The system further includes a control arrangement, such that the sensor which most accurately responds to a particular range of water vapor content is employed to indicate the water vapor content of the atmosphere being measured.

BACKGROUND OF THE INVENTION

There are many situations in which it is desirable or even necessary to determine the level of moisture in an atmosphere. For instance, in testing the permeability of a material to water vapor. One such instance is the testing of the water permeability of a plastic film or sheet used to form a package for a product. A test instrument is provided which passes a first water vapor containing atmosphere across one side of the plastic film or sheet and a second water vapor free atmosphere across the opposite side of the plastic film or sheet. Measurement of the water vapor level in the second atmosphere, after it has passed over the opposite side of the plastic film or sheet, provides an indication of the water vapor permeability of the plastic film or sheet. In such applications, the water vapor level in the second atmosphere will start out very low and increase as water vapor from the first atmosphere permeates the plastic film or sheet. Thus, it would be desirable to initially accurately read low levels of water vapor in the second atmosphere, and as more water vapor permeates the plastic film or sheet, thereafter read higher levels of water vapor in the second atmosphere. However, in other applications it is desirable to first measure high levels of water vapor, and thereafter measure lower levels. Such as, when it is desirable to monitor moisture being removed from an atmosphere and it is necessary to indicate when the moisture vapor level has reached a desired low level.

Separate systems and sensors have long been available to measure either high levels of water vapor or low levels of water vapor. However, a single testing apparatus and system has not been provided which will respond to water vapor levels in an atmosphere to accurately indicate both high levels of moisture vapor and low levels of moisture vapor, without the need to determine in advance whether high or low levels of water vapor are present in the atmosphere being observed. It has been necessary in the past to have prior knowledge of the water vapor level, since exposure of a typical low level water vapor sensor to other than a very short exposure to high moisture vapor levels would render it either inoperative, until it is dried, or even possibly destroy the sensor.

Accordingly, it would be of considerable advantage to provide a system and method in which a single instrument is provided to indicate both very low levels and also high levels of water vapor in an atmosphere without the need to first determine the water vapor level, so as not to expose a sensor for low levels of water vapor to a high level of water vapor, which would either destroy the sensor or render it inoperative until it is dried for a considerable period of time.

SUMMARY OF THE INVENTION

It is an object of this invention to provide a system and method for more efficiently sensing a wide range of moisture levels in an atmosphere. It is a further object of this invention to provide such a system and method which includes a pair of water vapor sensors, one of which is designed to measure high levels of water vapor and the other of which is designed to measure low levels of water vapor. It is still another object of this invention to provide such a system and method in which the flow path for the sample of atmosphere being sensed is controlled, such that the sensor responsive to low levels of water vapor is not exposed to high levels of water vapor for a period of time which would adversely affect its proper operation.

A system and method for detecting both high and low levels of water vapor in an atmosphere in accordance with this invention includes a pair of water vapor sensors, a first one of which sensors is sensitive to and measures high levels of water vapor, and a second one of which sensors is particularly sensitive to and measures low levels of water vapor. Alternate flow paths for the atmosphere being observed are provided, a first one passes the atmosphere through both the high and low level sensors, and a second which bypasses the second or low level sensor, and passes the atmosphere only through the first or high level sensor. When an atmosphere of unknown water vapor level is first supplied to the instrument it passes through the first flow path to be sensed by both sensors. However, if the water vapor level is higher than that which the low level sensor is designed to sense, the system will immediately switch to the second flow path which bypasses the low level sensor.

Alternatively, if the atmosphere initially provided to the system has a low level of water vapor, in the range of the low level sensor, the low level sensor will continue to sense the moisture level, until its normal measuring level is exceeded, in which case the system will switch to the second flow path, thereby bypassing the low level sensor. The flow path through the low level sensor is controlled by a pair of three-way valves, one of which is connected to the inlet of the low level sensor, and the other of which is connected to the outlet of the low level sensor. In a first position of the three-way valves the atmosphere flow path is through the low level sensor, and in a second position of the three-way valves the atmosphere flow path bypasses the low level sensor.

The system includes an electronic control circuit or system responsive to the output of the sensors to determine whether or not the low level sensor is to be bypassed, and to indicate the water vapor level measured by the high level sensor when the low level sensor is bypassed, and to indicate the water vapor level measured by the low level sensor when the atmosphere flows through the low level sensor. While many different types of three-way valves may be controlled by the electronic control circuit two types which may be used are reciprocating and rotary solenoid actuated valves.

DETAILED DESCRIPTION OF THE PREFERRED EMBODIMENT

Figure 1:
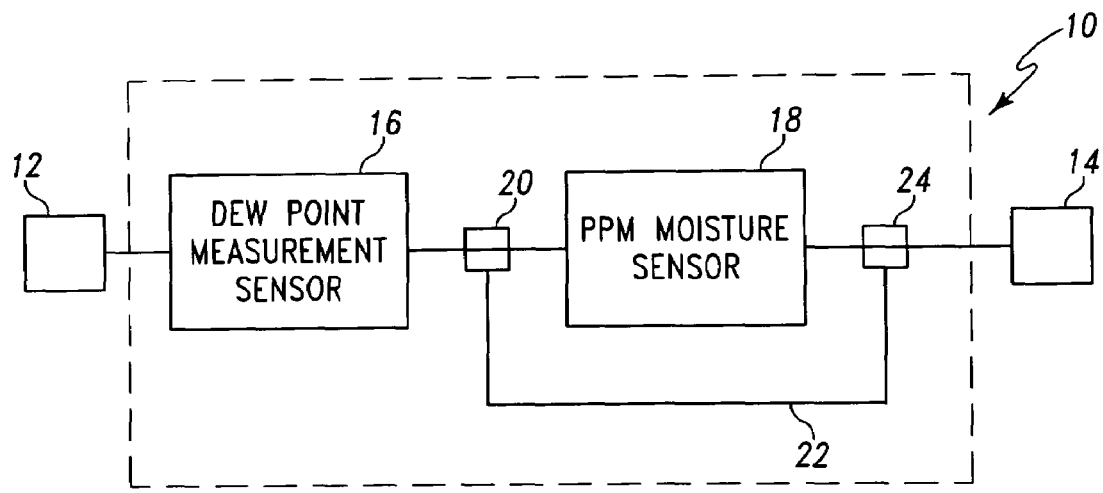
FIG. 1 is a flow diagram of a system for measuring a wide range of water vapor concentrations in an atmosphere in accordance with this invention.

Referring to FIG. 1, a dual sensor system 10 for measuring the presence of a wide range of water vapor concentration in an atmosphere is shown with an atmosphere inlet 12 and an outlet 14. The dual sensor system 10 includes a first sensor 16 which is designed to measure higher levels of water vapor concentrations, and a second sensor 18 which is designed to measure lower levels of water vapor concentrations. Using common terms for the first and second sensors, the first sensor 16 is labeled a Dew Point Measurement Sensor and the second sensor is labeled a PPM (parts-per-million) sensor. A sample of the atmosphere to be tested for water vapor concentration is first directed from inlet 12 to the first sensor 16. The first sensor 16 is selected such that it will readily measure larger concentration of water vapor in the sample atmosphere. Typical of water vapor sensors that could be used for the first sensor 16 are those which are identified as aluminum oxide, chilled mirror and infra red type dew point sensors. The sample atmosphere flows from the outlet of the first sensor 16 to a three-way valve. The three-way valve directs the sample atmosphere flow to either the input of the second sensor 18 through a first path or to a second or bypass flow path 22 which bypasses the second sensor 18 and then through a second three-way valve 24 which directs the flow to outlet 14. Three-way valves 20 and 24 are controlled to operate together, to provide either a first flow path through second sensor 18 or through the second or bypass flow path 22. Typical of water vapor sensors which could be used for the second sensor 18 are those which are identified as phosphorus pentoxide ($P_2O_5$) type moisture sensors.

Figure 2:
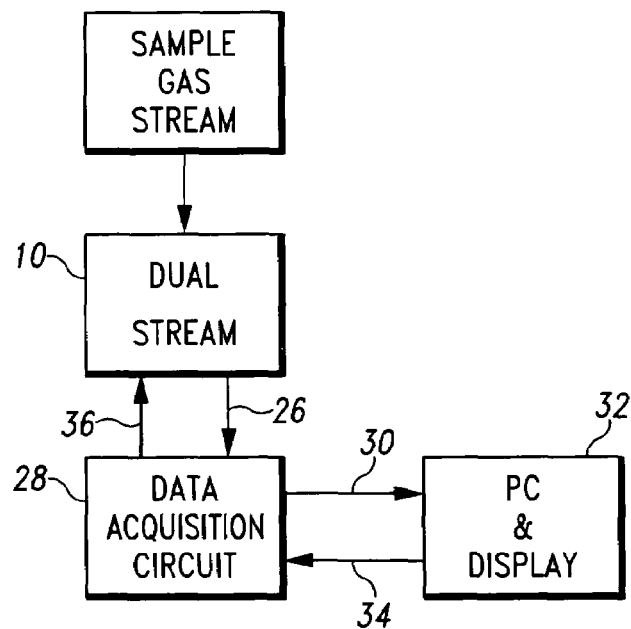
FIG. 2 is a block diagram of an electronic control system for use with the system and method for measuring a wide range of water vapor concentrations in an atmosphere in accordance with this invention.

Referring to FIG. 2, an electronic control arrangement for the dual sensor system and method of this invention for detecting and measuring a wide range of water vapor levels in an atmosphere will be described. As indicated in FIG. 2, a sample gas stream, the moisture content of which is to be measured, is provided to the dual sensor system 10. First and second electronic outputs from the first or dew point measurement sensor 16 and from the second or PPM sensor 18 respectively, indicative of the water vapor levels sensed by the sensors are supplied as indicated by the arrow 26 to a data acquisition circuit 28. A third output 30 from the data acquisition circuit 28 is supplied to a personal computer and display 32. The personal computer includes a software program which processes the output 30 received from the data acquisition circuit 28, and depending on the moisture levels sensed by the sensors 16 and 18 causes the personal computer 32 to develop a fourth output signal 34 which is provided to the data acquisition circuit 28, which in turn provides a fifth output signal 36 to the dual sensor system 10 to control the operation of the three-way valves 20 and 24. The software program of the personal computer 32 also causes the computer to provide an output to a display device which in turn displays the detected moisture level of the sample gas stream.

For a particular application of the system and method of this invention for sensing a wide range of water vapor levels in an atmosphere, the first sensor is designed to be responsive to water vapor or moisture levels in a range between 1,000 ppm and 23,000 ppm. The second sensor is designed to be responsive to water vapor or moisture levels in a range between 0.1 and 1000 ppm. Depending upon the application, first and second sensors having other ranges may be used, so long as the lower limit of the higher range sensor will indicate when the moisture level is below the upper limit of the lower range sensor.

Figure 3:
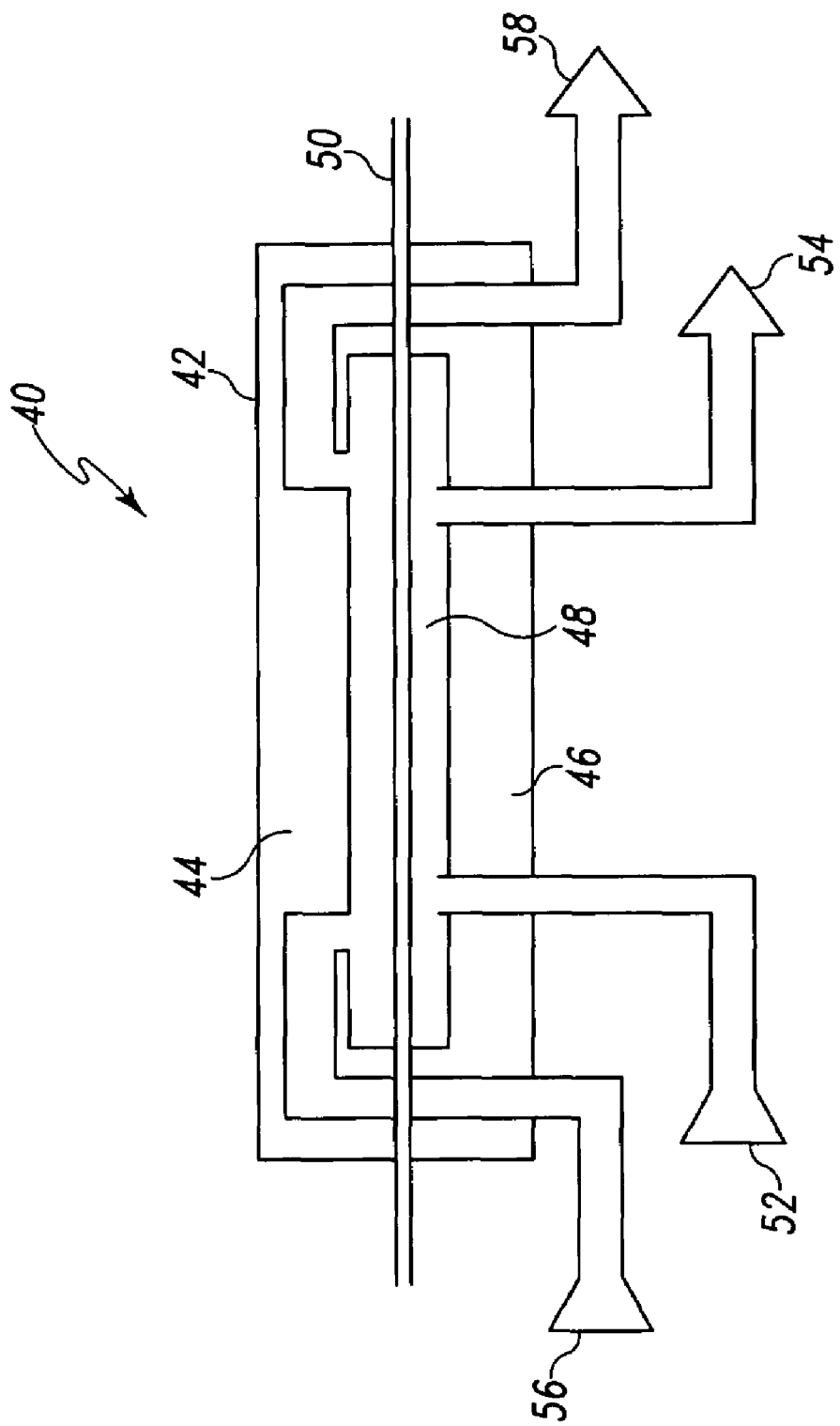
FIG. 3 shows a representation of a device for determining the water vapor permeability of a plastic film or sheet, which could utilize the system and method of this invention to indicate the water vapor permeability of a plastic film or sheet.

FIG. 3 provides a representation of a device for determining the water vapor permeability of a plastic film or sheet, which could utilize the system and method of this invention to indicate the water vapor permeability of the plastic film or sheet. The device 40, includes a housing 42 having two portions 44 and 46 which form a test chamber 48 through which a plastic film or sheet 50, the water vapor permeability of which is to be determined, extends. The chamber 48 exposes a predetermined area of a first side of the plastic film or sheet 50 to an atmosphere containing a predetermined level of water vapor. The water vapor laden atmosphere enters the chamber 48 on the upper side of the plastic film or sheet 50 through an inlet port 56 and exits through an outlet port 58. A moisture free atmosphere, such as dry $N^2$ is provided to the chamber 48 on the lower side of the plastic film or sheet 50 through an inlet port 52, and exits through an outlet port 54. Due to water vapor permeation of the plastic film or sheet 50 the dry $N^2$ atmosphere supplied to the lower side of the plastic film or sheet 50 through inlet port 52, picks up moisture before it exits the lower portion of chamber 48 through outlet port 54. The atmosphere exiting through outlet port 54 is supplied to the inlet 12 of the dual sensor system 10 on this invention. When use in this application, the water vapor level measurement will first be provided by the low level sensor, since initially no, or a miniscual amount of water vapor will appear in the atmosphere exiting through outlet port 54. As the moisture permeates through the plastic film or sheet 50, the water vapor level of the atmosphere provided to the dual sensor system 10 will increase, and may reach the level at which the low level moisture sensor 18 is bypassed, such that the moisture level measurement is provided by the high level moisture sensor 16.

While only one embodiment of the invention has been shown, it should be apparent to those skilled in the art that what has been described is considered at present to be a preferred embodiment of the system and method of this invention for providing a system and method for sensing a wide range of water vapor levels in an atmosphere. In accordance with the patent Statute, changes may be made in the system and method without actually departing from the true spirit and scope of this invention. The appended claims are intended to cover all such changes and modifications which fall in the true spirit and scope of this invention.

What is claimed is:

1. A system for sensing a wide range of water vapor levels in an atmosphere comprising:
    a first sensor for measuring high levels of water vapor in an atmosphere in a range between a first low limit and a first high limit, and for providing a first output signal,
    a second sensor for measuring low levels of water vapor in an atmosphere in a range between a second low limit and a second high limit, and for providing a second output signal,
    a first flow path for directing an atmosphere through said first and second sensors,
    a second flow path for directing the atmosphere through said first sensor and bypassing said second sensor, at least two three way valves jointly operable to direct said atmosphere through either said first flow path or said second flow path, a control device for receiving said first and second output signals from said first and said second sensors, and providing an output for controlling said at least two three way valves and an indication of the water vapor level of the atmosphere.

2. The system for sensing a wide range of water vapor levels of claim 1, wherein said control device will cause said at least two three way valves to direct the atmosphere through the second flow path when the water vapor level is greater than high limit of the range of the second sensor.

3. The system for sensing a wide range of water vapor levels of claim 1, wherein said control device will provide an output to said at least two three way valves, causing them to direct the atmosphere through the second flow path when the water vapor level is greater than high limit of the range of the second sensor.

4. The system for sensing a wide range of water vapor levels of claim 1, wherein said at least two three way valves are solenoid operated rotary valves.

5. The system for sensing a wide range of water vapor levels of claim 1, wherein said at least two three way valves are solenoid operated reciprocating valves.

6. The system for sensing a wide range of water vapor levels of claim 1, wherein said high limit of the range of the second sensor is within the range of the first sensor.

7. The system for sensing a wide range of water vapor levels of claim 1, wherein said second sensor is a phosphorus pentoxide ($P_2O_5$) type sensor.

8. The system for sensing a wide range of water vapor levels of claim 1, wherein said first sensor is selected from the group consisting of aluminum oxide, chilled mirror and infra red type dew point sensors.

9. The system for sensing a wide range of water vapor levels of claim 1, wherein said first sensor is responsive to water vapor levels in a range generally between 1,000 parts/per/million and 23,000 parts/per/million.

10. The system for sensing a wide range of water vapor levels of claim 1, wherein said second sensor is responsive to water vapor levels in a range generally between 0.1 parts/per/million and 1,000 parts/per/million.

11. The system for sensing a wide range of water vapor levels of claim 1, wherein if said control device receives a first output signal indicating that said water vapor level is within a range between the first low limit and the first high limit, said control device will cause said at least two three way valves to direct the atmosphere through the second flow path.

12. A system for sensing a wide range of water vapor levels in an atmosphere comprising:

a first sensor for measuring high levels of water vapor in an atmosphere in a range between a first low limit and a first high limit, and for providing a first output signal, a second sensor for measuring low levels of water vapor in an atmosphere in a range between a second low limit and a second high limit, and for providing a second output signal, a first flow path for directing an atmosphere through said first and second sensors, a second flow path for directing the atmosphere through said first sensor and bypassing said second sensor, at least two three way valves jointly operable to direct said atmosphere through either said first flow path or said second flow path, a data acquisition circuit for receiving said first and second output signals from said first and said second sensors, and providing a third output signal, a computer having a software program which processes the third output signal from said data acquisition circuit, and which provides a fourth output signal to said data acquisition circuit, which provides a fifth output signal to control said at least two three way valves to direct the atmosphere through either said first or second flow path, said computer providing an output to a display device which indicates the detected moisture vapor level of the atmosphere.

* * * * *